United States Patent [19]

Pressman et al.

[11] Patent Number: 5,414,151
[45] Date of Patent: May 9, 1995

[54] METHOD FOR MAKING BISPHENOL

[75] Inventors: Eric J. Pressman, East Greenbush; Sheldon J. Shafer, Clifton Park, both of N.Y.

[73] Assignee: General Electric Company, Schenectady, N.Y.

[21] Appl. No.: 236,816

[22] Filed: May 2, 1994

[51] Int. Cl.⁶ .................. C07C 37/20; C07C 39/16
[52] U.S. Cl. ...................... 568/727; 568/722; 568/728
[58] Field of Search ............... 568/722, 727, 728, 723

[56] References Cited

U.S. PATENT DOCUMENTS

| 3,394,089 | 7/1968 | McNutt et al. | 521/32 |
| 3,634,341 | 1/1972 | Gammill et al. | 521/32 |
| 3,760,006 | 9/1973 | Gammill et al. | 568/727 |
| 4,294,995 | 10/1981 | Faler et al. | 568/728 |
| 4,346,247 | 8/1982 | Faler et al. | 568/728 |
| 4,396,728 | 8/1983 | Faler | 521/32 |
| 4,424,283 | 1/1984 | Faler et al. | 521/32 |
| 4,455,409 | 6/1984 | Faler et al. | 525/351 |
| 4,584,416 | 4/1986 | Pressman et al. | 568/727 |
| 4,918,245 | 4/1990 | Iimuro et al. | 568/728 |
| 5,284,981 | 2/1994 | Rudolph et al. | 568/727 |
| 5,302,774 | 4/1994 | Berg et al. | 568/727 |

FOREIGN PATENT DOCUMENTS

| 0567857 | 11/1993 | European Pat. Off. | 568/727 |
| 1231991 | 1/1968 | United Kingdom . | |
| 1183564 | 5/1968 | United Kingdom . | |

Primary Examiner—Werren B. Lone
Attorney, Agent, or Firm—William A. Teoli; William H. Pittman

[57] ABSTRACT

A method is provided for making bisphenol by condensing a ketone and a phenol in the presence of a sulfonated aromatic organic polymeric ion-exchange catalyst having aminoorganomercaptan groups using a phenol having less than 1 ppm of hydroxyacetone.

7 Claims, 1 Drawing Sheet

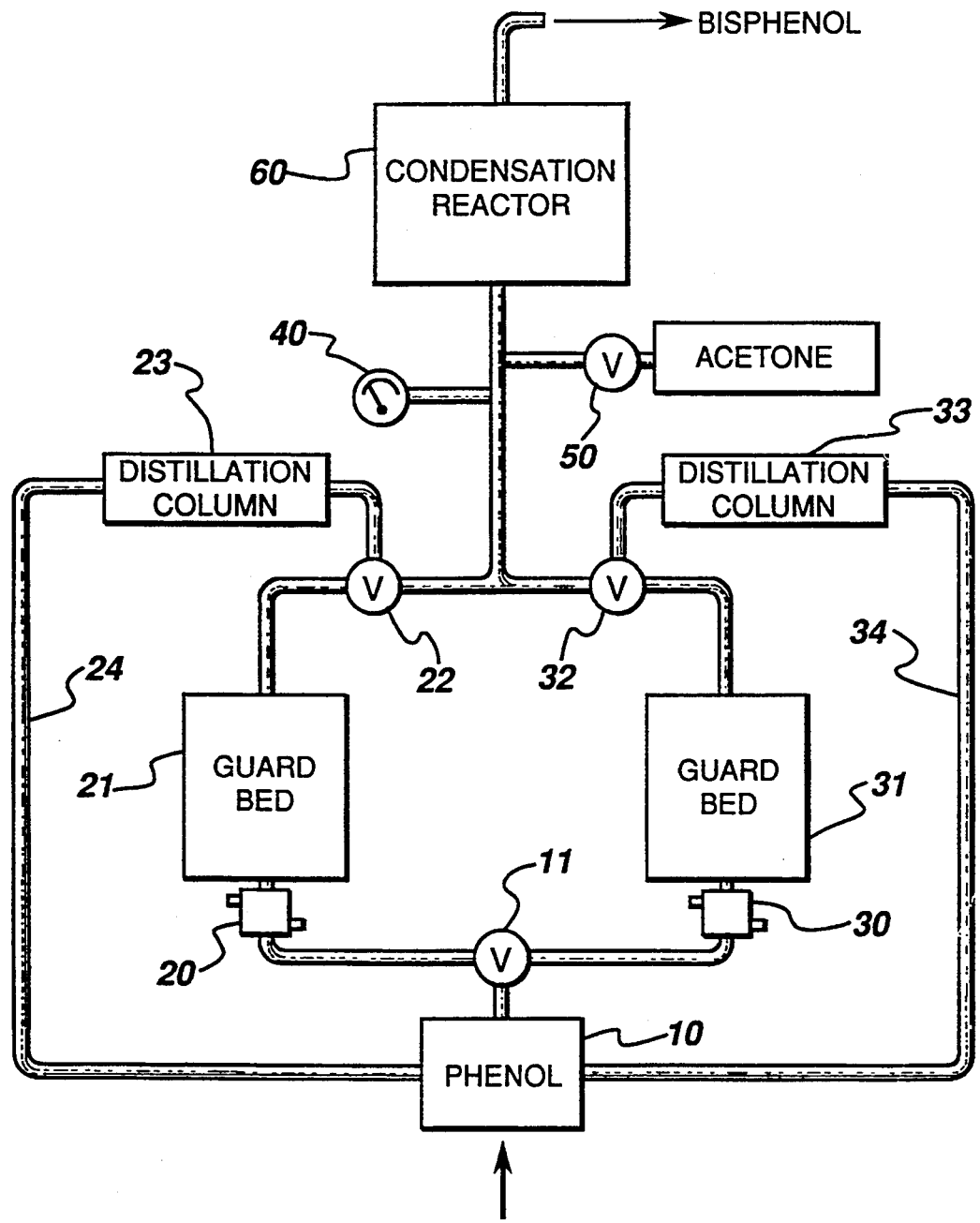

METHOD FOR MAKING BISPHENOL

CROSS REFERENCE TO RELATED APPLICATION

Reference is made to copending application RD-23171 filed concurrently herewith.

BACKGROUND OF THE INVENTION

The present invention relates to a method for making a bisphenol, such as bisphenol A(BPA), by the condensation of a phenol, and a ketone in the presence of a sulfonated aromatic organic polymer, such as a polystyrene ion-exchange resin having chemically combined aminoorganomercaptan groups. More particularly, the present invention relates to a condensation reaction between acetone and a phenol reactant which has been initially fed through an ion-exchange "guard bed" in the form of a sulfonated polystyrene ion-exchange resin having chemically combined aminoorganomercaptan groups, prior to the subsequent condensation of the phenol with acetone.

As discussed in British patent 1,183,564, which is incorporated herein by reference, an improvement can be achieved in the synthesis of bisphenol A by the condensation of phenol with acetone, if an ion-exchange catalyst is used which contains sulfonic acid groups. As shown by Pressman et al., U.S. Pat. No. 4,584,416 which is incorporated herein by reference, an ion-exchange resin in the form of a sulfonated polystyrene having ionically bound aminoorganomercaptan groups can be used as a catalyst to make bisphenol. As used hereinafter, the expression "chemically combined" which is sometimes used with reference to aminoorganomercaptan groups, means that these groups can be either ionically or covalently bound to the backbone of the sulfonated aromatic organic polymeric resin. As taught by Pressman et al., improved acetone conversion and p,p-bisphenol A selectivity can be achieved with the use of sulfonated aromatic organic polymeric ion-exchange resin having chemically combined aminoorganomercaptan groups Experience has shown however, that the activity of a sulfonated polystyrene ion-exchange resins having such chemically combined aminoorganomercaptan groups is often adversely affected over a period of time. A reduction in chemically combined aminoorganomercaptan, or "thiol" groups can result. A possible explanation of the loss of thiol groups in the sulfonated polystyrene resin is that the phenol which is used in the condensation reaction with acetone can be contaminated with greater than 1 ppm of hydroxyacetone (HA). The hydroxyacetone has been found to directly react with aminoorganomercaptan groups to form a substantially stable species having reduced catalytic activity. As a result, a dramatic decrease in rate of bisphenol A production can result over a period of time.

It would be desirable therefore to maintain the activity of the bisphenol condensation catalyst. It also would be desirable to minimize the deactivation of chemically combined aminoorganomercaptan groups and achieve a satisfactory rate of bisphenol production.

SUMMARY OF THE INVENTION

The present invention is based on the discovery that improved bisphenol production and an extension in the life of the bisphenol condensation catalyst can be achieved by using as the phenol reactant, a material having less than about 1 ppm of hydroxyacetone(HA). Experience has shown that the employment of a substantially hydroxyacetone free phenol reactant in the condensation reaction can result in an extension of the life of the bisphenol ion-exchange resin condensation catalyst.

It has been further found, that if the phenol reactant is initially passed through a sulfonated aromatic organic polymeric ion-exchange resin, referred to hereinafter sometimes as a "guard bed" having chemically combined aminoorganomercaptan groups, before the phenol reactant is condensed with acetone, a substantial decrease in the deactivation of aminoorganomercaptan groups on the ion-exchange condensation catalyst can be realized. As a result, a significant reduction in the rate of the deactivation of the ion-exchange condensation catalyst can be achieved by minimizing the formation of the hydroxyacetone modified aminoorganomercaptan group. The life of the bisphenol ion-exchange condensation catalyst therefore can be substantially improved.

STATEMENT OF THE INVENTION

There is provided by the present invention, a condensation process for making bisphenol which comprises effecting reaction between a phenol reactant and a ketone in the presence of a sulfonated aromatic organic polymeric ion-exchange resin having chemically combined organo mercaptan groups attached to backbone sulfonate radicals, where there is used as the phenol reactant, a phenolic effluent produced by passing phenol through an ion-exchange resin comprising a sulfonated aromatic organic polymeric ion-exchange resin having organo mercaptan groups attached to backbone sulfonate radicals until the resulting phenolic effluent has more than about 1 ppm of hydroxyacetone.

Reference is made to the schematic drawing of a BPA reaction system having a phenol source, and an acetone source which are fed into a bisphenol condensation reactor. Two phenol purification systems which include ion-exchange guard beds are also shown. The guard beds consist respectively of an aromatic organic polymeric ion-exchange resin having organo mercaptan groups attached to backbone sulfonate radicals; each guard bed is combined with a distillation column, to effect the separation of phenol from "heavies" and a return to the phenol source. An exit duct for bisphenol generated from the reactor is also shown. All systems are operated through a series of valves.

More particularly, phenol is fed from a source at 10 through valve 11 to a heating coil at 20 or 30 and thereafter to an ion-exchange resin guard bed, at 21 or 31 to provide a phenol effluent having from about 0 to up to about 1 ppm of hydroxyacetone. The phenol effluent is initially fed through valve 22 or 32 to the condensation reactor at 60 providing its HA is less than 1 ppm. Acetone is fed through valve 50. The ion-exchange resin reactor at 60 effects condensation between phenol and acetone at a temperature of about 40° C. to about 120° C. to produce bisphenol.

During the course of feeding phenol through ion-exchange resin guard bed 21 or 31, the guard bed can become deactivated which results from the presence of greater than 1 ppm of hydroxyacetone (HA). The level of HA can be by monitored at meter 40. At this point, the deactivated guard bed can be shut down using valves 11 and 22, or valves 11 and 32 and the alternate guard bed can be used. Restoration of the deactivated guard bed can proceed by passage of heated anhydrous phenol through the bed until high pressure liquid chromatography (HPLC) shows less than about 1 ppm of a phenolic trisphenol reaction product in the resulting effluent. The trisphenol or an isomer thereof, is shown in copending application RD-23,171. Washing of the deactivated guard bed with anhydrous phenol (less than 100 ppm of water) at temperatures of 70° C. to 120° C. has been found to restore deactivated aminoorganomercaptan groups to produce phenolic products which can be eluted from the insoluble sulfonic acid resin sites.

The ion-exchange resin which is used in the BPA resin bed is a sulfonated aromatic organic polymer having from about 4 to 40 mole percent of ionically bound aminoorganomercaptan groups of the formula,

(1)

where R is a $C_{(2-10)}$ divalent organo radical, and $R^1$ is a monovalent radical selected from hydrogen or a $C_{(1-8)}$ alkyl radical.

There are included by the $C_{(2-10)}$ organo radicals of R of formula (1) divalent $C_{(2-10)}$ aliphatic radicals, such as mono substituted trimethylene, tetramethylene, pentamethylene, hexamethylene; aromatic radicals, such as mono substituted phenylene, xylylene, tolylene, naphthylene, etc. R also includes aliphatic and aromatic radicals as previously defined, which are further substituted with halogen radicals, for example, chloro, bromo, fluoro, etc. There are included by $R^1$ radicals of formula (1) monovalent alkyl radicals, such as methyl, ethyl, propyl, butyl, pentyl, hexyl, heptyl and octyl.

Some of the sulfonated aromatic organic polymer which can be used in the practice of the present invention having ionically bound alkylaminoorganomercaptan groups of formula (1) can be made by procedures shown by Faler, U.S. Pat. No. 4,396,728 and Pressman et al. U.S. Pat. No. 4,584,416 which are incorporated herein by reference. Additionally, covalently bound ion-exchange resin also can be used as shown by Faler et al., U.S. Pat. No. 4,455,409, also incorporated herein by reference.

Phenols which can be used in the practice of the present invention to make bisphenol include, for example, phenol and substituted phenols, such as

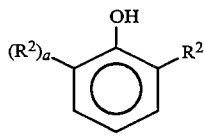

where $R^2$ is a monovalent $C_{(1-8)}$ alkyl radical, for example, methyl, ethyl, propyl, etc., and a is equal to 0 to 1.

Ketones which can be employed in the practice of the present invention to make bisphenols are, for example, acetone, diethylketone, methylethylketone, cyclohexanone, acetophenone, etc.

Some of the ion-exchange resins of the present invention can be prepared by effecting reaction between sulfonated aromatic organic polymer and N-alkylaminoorganomercaptan monomer which can be in the form of the hydrohalide or corresponding hydrotosylate. A convenient synthesis of the N-alkylaminoorganomercaptan hydrotosylate, for example, can involve an initial reaction between a bromochloroalkane and an alkali metal thiosulfate which can be refluxed in an inert atmosphere in an organic solvent, such as aqueous methanol. There can be added to the resulting reaction mixture an appropriate alkyl amine which can be further refluxed. Methanol and excess alkyl amine can be distilled from the mixture and isopropanol added to remove the water by azeotropic distillation. The alkylaminoorganothiosulfate and by-product alkali metal halide can then be isolated free of water by filtration of the isopropanol slurry.

A mixture of methanol and the above alkylaminoorganothiosulfate and paratoluenesulfonic acid monohydrate can be refluxed under nitrogen, followed by a standard organic extraction and work up which provides the desired product in a chlorinated hydrocarbon solvent. The tosylate salt can then be precipitated by addition of an appropriate aliphatic hydrocarbon solvent and isolated by filtration.

The ion-exchange resin catalyst of the present invention having ionically bound N-alkylaminoorganomercaptan groups can be made by effecting reaction between the sulfonated aromatic organic polymer and the N-alkylaminoorganomercaptan salt in the form of a halide salt or tosylate salt as described above. The sulfonated aromatic organic polymer in the form of a dry resin can be initially analyzed for sulfonic acid content by a standard neutralization technique and typically contains 22.1 millimoles of sulfonic acid groups per 4.70 grams of dry resin. An appropriate amount of the hydrohalide or hydrotosylate salt of the aminoorganomercaptan (typically 0.25 equivalents relative to sulfonic acid groups on the base resin) is stirred as an aqueous solution in the presence of the base resin. The mixture can be heated at a temperature in the range of from room temperature to 70° C. for 4 hours while being slowly agitated and thereafter allowed to cool to room temperature. The resulting ion-exchange catalyst can thereafter be filtered, washed with water, and then vacuum oven dried.

The percent nitrogen in the ion-exchange catalyst can be determined using a Carlo Erba nitrogen analyzer. From this data, nitrogen milliequivalency/gram of dry catalyst can be determined which shows the fraction of total sulfonic acid sites occupied by N-alkylaminoorganomercaptan groups of formula (1). Mercaptan milliequivalency/per gram of dry catalyst can be determined using Ellman's reagent (A. Fontant and C. Toniolo, The Chemistry of the Thiol Group, S. Patai, Editor, John Wiley and Sons, Ltd., London (1979), pp. 288–290).

With respect to the preparation of bisphenols utilizing sulfonated aromatic organic polymer containing N-alkylaminoorganomercaptan groups of the present invention, a mixture of phenol and ketone can be heated in the presence of the cation-exchange resin prepared in accordance with the practice of the present invention. There can be utilized 2–20 moles of the phenol per mole of the ketone which can be heated at a temperature in the range of from 50° C. to 110° C., with agitation. The ion-exchange resin can be employed at from 0.1% to 10% by weight, based on the weight of the total mixture in instances where a batch process is used. In a preferred procedure for making bisphenol in a continuous manner, the ion-exchange resin can be used in a column which can be operated at a temperature of 50° C. to 100° C. The mole ratio of reactants can vary widely, such as from about 3 to 1 to about 20 to 1 moles of phenol per mol of ketone. It is preferred, however, to use the reactants at a mole ratio of about 4 to 1 to about 12 to 1 moles of phenol per mol of ketone.

One method of recovering the bisphenol reaction product, for example, bisphenol-A, is by crystallizing the BPA/phenol adduct from the reactor effluent and recovery of the bisphenol A by distillation or crystallization. Other procedures are, for example, distillation of the reaction mixture to separate the phenol and bisphenol or partial distillation to remove the phenol followed by recrystallization of the residual bisphenol using water, methanol, acetonitrile, methylene chloride or toluene as the solvent. A crystallization procedure for BPA recovery is also shown by G. R. Faler, U.S. Pat. No. 4,375,567, assigned to the same assignee as the present invention and incorporated herein by reference.

In order that those skilled in the art will be better able to practice the invention, the following example is given by way of illustration and not by way of limitation. All parts are by weight.

Example

A sulfonated polystyrene having about 20 mole percent of ionically bound 2-aminoethanethiol (20% of acid sites) was prepared in accordance with the procedure of Pressman et al., U.S. Pat. No. 4,584,416. Amberlite 118 (polystyrene sulfonic acid resin crosslinked with 4% divinylbenzene (DVB) was modified with 2-aminoethanethiol (20% of acid sites).

Commercially available phenol was obtained and analyzed by gas chromatography for hydroxyacetone. The phenol was distilled by removing about 10% by volume of initial distillate. Purification of the phenol also was effected by elution through the above modified sulfonated polystyrene resin (feed=phenol; WHSV=10g feed*g$^{-1}$catalyst*hr$^{-1}$;70° C.). The following results were obtained where HA is hydroxyacetone:

TABLE 1

| HA Levels in Various Phenol Samples | |
|---|---|
| Sample | ppm HA |
| Unpurified phenol | 19 |
| Distilled phenol | 8 |
| Purified phenol | <1 |

An 8:1 molar mixture of phenol and acetone having 7.16% of acetone by weight was continuously fed at a rate of 140 g/hr (WHSV-20) through 7.0 g of the above 2-aminoethanethiol modified sulfonated polystyrene. The reaction was continued for a period of 100 hrs. The output stream from the bed was monitored by HPLC to calculate percent acetone converted to p,p BPA. It was found that after 24 hrs, there was obtained about a 42% conversion of the acetone. However, a dramatic difference was observed after 100 hrs with phenol which had been purified by pretreatment with the above 2-aminoethanethiol modified sulfonated polystyrene (39% conversion)as compared to untreated, commercially available phenol (31% conversion).

The aminoethanethiol content of 2-aminoethanethiol modified sulfonated polystyrene resins were also determined by the HPLC analysis of a benzoylated aliquot of a sample stripped from the respective sulfonic acid resin. The following table compares the unused resin (virgin) with resin analyzed after 100 hrs reaction with purified and unpurified phenol:

TABLE 2

| Aminoethanethiol Content in Catalysts After 100 Hrs. of Continuous Reaction | |
|---|---|
| Catalyst | meq $H_2NCH_2CH_2SH$/gram |
| Virgin | 0.860 |
| After unpurified phenol usage | 0.368 |
| After purified phenol usage | 0.750 |

The above results show a significant improvement in catalyst stabilization resulting from purified phenol usage.

Although the above example is directed to only a few of the many variables which can be used in the practice of the present invention, it should be understood that the present invention is directed to a much greater variety of ion-exchange resins, phenols, and ketones, as set forth in the description preceding this example.

What is claimed is:

1. A condensation process for making bisphenol, which comprises effecting reaction between a phenol reactant and a ketone in the presence of a sulfonated aromatic organic polymeric ion-exchange resin having chemically combined organo mercaptan groups attached to backbone sulfonate radicals, where there is used as the phenol reactant, a material produced by passing phenol through an ion-exchange resin comprising a sulfonated aromatic organic polymeric ion-exchange resin having organo mercaptan groups attached to backbone sulfonate radicals until the resulting phenolic effluent has more than about 1 ppm of hydroxyacetone.

2. A condensation process in accordance with claim 1, where the sulfonated aromatic polymeric organic ion-exchange resin is a sulfonated polystyrene.

3. A condensation process in accordance with claim 1, where the aminoorganomercaptan groups are covalently bonded.

4. A condensation process in accordance with claim 1, where the aminoorganomercaptan groups are ionically bonded.

5. A condensation process in accordance with claim 1, where the phenolic effluent is produced by passing phenol through an ion-exchange resin guard bed.

6. A condensation process in accordance with claim 1, where the ketone is acetone.

7. A condensation process for making bisphenol A, which comprises effecting reaction between a phenol reactant and a acetone in the presence of a sulfonated aromatic organic polymeric ion-exchange resin having chemically combined organo mercaptan groups attached to backbone sulfonate radicals, where there is used as the phenol reactant, a material produced by passing phenol through an ion-exchange resin comprising a sulfonated aromatic organic polymeric ion-exchange resin having organo mercaptan groups attached to backbone sulfonate radicals until the resulting phenolic effluent has more than about 1 ppm of hydroxyacetone.

* * * * *

UNITED STATES PATENT AND TRADEMARK OFFICE
CERTIFICATE OF CORRECTION

PATENT NO.    : 5,414,151
DATED         : May 9, 1995
INVENTOR(S)   : Eric J. Pressman and Sheldon J. Shafer It is certified that error appears in the above-identified patent and that said Letters Patent is hereby corrected as shown below:

Column 2,
Line 37, "has more than" should read -- has less than --.

Column 6,
Line 35, "has more than" should read -- has less than --.
Line 54, "a acetone" should read -- acetone --.
Line 63, "has more than" should read -- has less than --.

Signed and Sealed this

Eighteenth Day of March, 2003

JAMES E. ROGAN
*Director of the United States Patent and Trademark Office*